(12) United States Patent
Zoller et al.

(10) Patent No.: US 7,528,155 B2
(45) Date of Patent: May 5, 2009

(54) INDAZOLE DERIVATIVES AS INHIBITORS OF HORMONE SENSITIVE LIPASE

(75) Inventors: Gerhard Zoller, Schoneck (DE); Stefan Petry, Kelkheim (DE); Gunter Muller, Sulzback a. Ts. (DE); Hubert Heuer, Schwabenheim (DE); Karl-Heinz Baringhaus, Wolfersheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 440 days.

(21) Appl. No.: 11/042,565

(22) Filed: Jan. 25, 2005

(65) Prior Publication Data

US 2005/0197348 A1 Sep. 8, 2005

Related U.S. Application Data

(60) Provisional application No. 60/582,669, filed on Jun. 24, 2004.

(30) Foreign Application Priority Data

Feb. 2, 2004 (DE) .................. 10 2004 005 172

(51) Int. Cl.
A61K 31/454 (2006.01)
(52) U.S. Cl. ...................... 514/322; 546/199
(58) Field of Classification Search ................ 546/120, 546/199; 514/322
See application file for complete search history.

(56) References Cited

U.S. PATENT DOCUMENTS

| | | | |
|---|---|---|---|
| 4,051,252 A | 9/1977 | Mayer et al. | |
| 5,190,923 A | 3/1993 | Vincent et al. | |
| 5,665,732 A | 9/1997 | Baker et al. | |
| 5,739,135 A * | 4/1998 | Biller et al. ............ | 514/252.03 |
| 6,011,159 A | 1/2000 | Caron et al. | |
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,342,512 B1 | 1/2002 | Kirsch et al. | |
| 6,410,652 B1 | 6/2002 | Glodblatt et al. | |
| 6,624,185 B2 | 9/2003 | Glombik et al. | |
| 6,635,655 B1 | 10/2003 | Jayossi et al. | |
| 2006/0069255 A1 * | 3/2006 | Valgeirsson et al. ......... | 544/224 |

FOREIGN PATENT DOCUMENTS

| | | |
|---|---|---|
| GB | 681376 * | 10/1952 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/64876 | 11/2000 |
| WO | WO 00/66585 | 11/2000 |
| WO | WO 00/71549 | 11/2000 |
| WO | WO 00/78312 | 12/2000 |
| WO | WO 01/09111 A1 | 2/2001 |
| WO | WO 01/83451 | 11/2001 |
| WO | WO 03/035005 | 5/2003 |
| WO | WO 03/068773 | 8/2003 |
| WO | WO 03/097610 | 11/2003 |
| WO | WO 2004/022544 | 3/2004 |
| WO | WO 2004/046090 | 6/2004 |
| WO | WO 2004046090 A2 * | 6/2004 |
| WO | WO 2004/062662 | 7/2004 |
| WO | WO 2004093872 A1 * | 11/2004 |

OTHER PUBLICATIONS

Johnson, A. W. Invitation to Organic Chemistry 1999 Jones and Bartlett: Mississauga, Canada, p. 24.*
Lowe et. al. "In vitro SAR of (5-(2H)-isoxazonlonyl) ureas, potent inhibitors of hormone-sensitive lipase" Bioorganic & Medicinal Chemistry Letters 2004, 14, 3155-3159.*
Ebdrup et. al. "Synthesis and Structure-Activity Relationship for a Novel Class of Potent and Selective Carbamoyl-Triazole Based Inhibitors of Hormone Sensitive Lipase" Journal of Medicinal Chemistry 2004, 47, 400-410.*
Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.
Baiocchi. et. al., Synthesis, Properties, and Reactions of 1 H-Indazol-3-ols and 1,2-Dihydro-3H-indazol-3-ones, Synthesis (1978) pp. 633-648.

(Continued)

*Primary Examiner*—Janet L Andres
*Assistant Examiner*—David K O'Dell
(74) *Attorney, Agent, or Firm*—Barbara E. Kurys

(57) ABSTRACT

The present invention relates to indazole derivatives of the general formulae I or II having the meanings indicated in the description, to the pharmaceutically useful salts thereof and the use thereof as drugs.

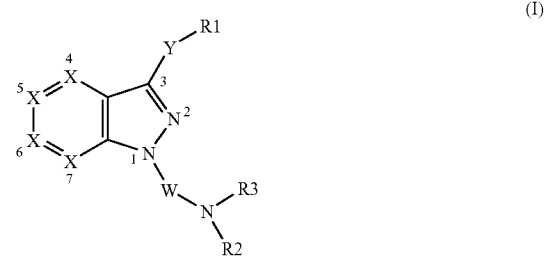

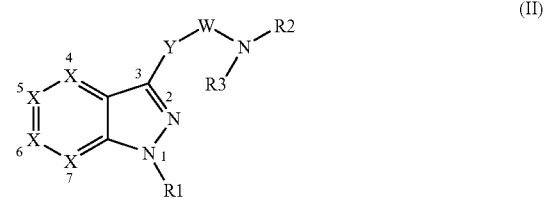

5 Claims, No Drawings

OTHER PUBLICATIONS

Fredrikson G et al, Hormone-sensitive Lipase of Rat Adipose Tissue, J. Biol. Chem., 1981, vol. 256, No. 12, pp. 6311-6320.

Lee Daniel W et al., Leptin agonists as a potential approach to the treatment of obesity, Drugs of the Future, 2001, vol. 26(9), pp. 873-881.

Nilsson S et al., Purification of Hormone-Sensitive Lipase by High-Performance Ion Exchange Chromatography, Anal. Biochem., 1986, vol. 158, pp. 399-407.

Okada Hiroshi et al., Synthesis and Antitumor Activities of Prodrugs of Benzoylphenylureas, Chem. Pharm. Bull., 1994, vol. 42(1), pp. 57-61.

Salvador Javier et al., Perspectives in the Therapeutic Use of Leptin, Expert Opinion Pharmacotherapy, (2001), vol. 2, No. 10, pp. 1615-1622.

Sekikawa et. al., Antituberculous Compounds XXVIII. Synthesis of Pyrazolopyridines, Research Institute for Tuberculosis, Hokkaido University, Sapporo, Japan (1973) pp. 931-932.

Tornqvist H et al., Purification and Some Properties of a Monoacylglycerol-hydrolyzing Enzyme of Rat Adipose Tissue, J. Biol. Chem., 1976, vol. 251, No. 3, pp. 813-819.

Tyle Praveen, Iontophoretic Devices for Drug Delivery, Pharmaceutical Research, 1986, vol. 3, No. 6, 318-326.

Zunft, H. et al., Carob Pulp Preparation for Treatment of Hypercholesterolemia, Advances in Therapy, 2001, vol. 18(5), pp. 230-236.

Lan, R., et. al., Structure-Activity Relationships of Pyrazole Derivatives as Cannabinoid Receptor Antagonists, Journal of Medicinal Chemistry, American Chemical Society (1999) vol. 42, pp. 769-776.

* cited by examiner

INDAZOLE DERIVATIVES AS INHIBITORS OF HORMONE SENSITIVE LIPASE

The present invention relates to indazole derivatives of the general formulae I or II, the pharmaceutically usable salts thereof and the use thereof as drugs.

Indazole derivatives for stimulating the cannabinoid receptor are described in WO 03/035005 and derivatives of 3-amino-indazole carboxylic acid in DE 24 58 965. Furthermore phenyl carbamoyl-indazole derivatives are described in WO 2004/046090 and 3-amino 5-phenyl-indazole-1-carboxylic acid amide in US 2004/0097485, which however have been published after the filing date of the priority application.

The invention relates to indazole derivatives of the general formulae I or II,

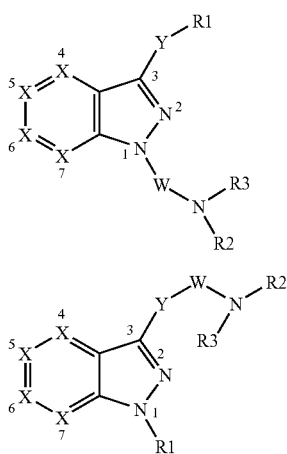

in which the meanings are:

W is —(C=O)—, —(S=O)— or —(SO$_2$)—;
X is =C(—R)— or =N—;
Y is —O— or —N(R1);
R is hydrogen, halogen, (C$_1$-C$_6$)-alkyl, (C$_1$-C$_3$)-alkyloxy-(C$_1$-C$_3$)-alkylene, hydroxy, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, COOR4, cyano, trifluoromethyl, (C$_1$-C$_6$)-alkylsulfonyl, (C$_1$-C$_6$)-alkylsulfinyl, aminosulfonyl, nitro, pentafluorosulfanyl, (C$_6$-C$_{10}$)-aryl, (C$_5$-C$_{12}$)-heteroaryl, CO—NR2R3, O—CO—NR2R3, O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—NR2R3 or unsubstituted or mono- or poly-F-substituted (C$_1$-C$_6$)-alkyloxy;
R1 is H, (C$_1$-C$_6$)-alkyl or benzyl;
R2 is H, (C$_1$-C$_6$)-alkyl, (C$_1$-C$_4$)-alkyl-phenyl or (C$_6$-C$_{10}$)-aryl, wherein said (C$_1$-C$_4$)-alkyl-phenyl or (C$_6$-C$_{10}$)-aryl is optionally substituted by halogen, (C$_1$-C$_6$)-alkyl, (C$_1$-C$_3$)-alkyloxy, hydroxy, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, (C$_1$-C$_6$)-alkoxycarbonyl, cyano, trifluoromethyl, trifluoromethoxy, (C$_1$-C$_6$)-alkylsulfonyl, aminosulfonyl, nitro or tetramethyl-tetrahydronaphthalene;
R3 is H or (C$_1$-C$_6$)-alkyl; or
R2 and R3 may form together with the nitrogen atom carrying them a monocyclic, saturated or partially unsaturated 4- to 7-membered ring system or a bicyclic saturated or partially unsaturated 8- to 14-membered ring system, whose individual members of the ring systems may be replaced by one to three atoms or atomic groups from the series —CHR5-, —CR5R5-, —(C=R5)-, —NR5-, —C(=O)—, —O—, —S—, —SO—, —SO$_2$—, with the proviso that two units from the series —O—, —S—, —SO—, —SO$_2$— may not be adjacent;
R4 is hydrogen, (C$_1$-C$_6$)-alkyl or benzyl;
R5 is (C$_1$-C$_6$)-alkyl, halogen, trifluoromethyl, COOR4, cyclopropyl or cyclopropylene;

and the physiologically tolerated salts thereof as well as its tautomeric forms with the proviso that in compounds of the formula (I) with W=CO
a) R2 and R3 together with the nitrogen atom carrying them form a monocyclic or bicyclic ring system if Y=N(R1) with R1=H or (C$_1$-C$_6$)-alkyl or
b) YR1, R2 and R3 do not have simultaneously the following meanings: YR1=OH, R2=(C$_6$-C$_{10}$)-aryl which may be substituted and R3=H.

Preferred compounds of the formulae I and II are those in which
Y is —O—,
or those in which
W is —(C=O)—.

Preferred compounds of the formulae I and II are further those in which
NR2R3 is a monocyclic saturated 5- to 6-membered ring system comprising in position 4 an atom or atomic member from the series —CHR5-, —CR5R5-, —(C=R5)-, —NR5-, —O—, —S—.

Further preferred compounds of the formulae I and II are those in which
X in position 4, 5 and 7 is =C(—R)— with R=hydrogen.
Particularly preferred compounds of the formula I or II are those in which
W is —(C=O)—;
X is =C(—R)— or =N—;
Y is —O—;
R is hydrogen, halogen, (C$_1$-C$_6$)-alkyl, hydroxy, amino, COOR4, trifluoromethyl, (C$_1$-C$_6$)-alkylsulfonyl, nitro, pentafluorosulfanyl, (C$_6$-C$_{10}$)-aryl, CO—NR2R3, O—CO—NR2R3 or O—CO—(C$_1$-C$_6$)-alkylene-CO—O—(C$_1$-C$_6$)-alkyl;
R1 is H, (C$_1$-C$_6$)-alkyl or benzyl;
R2 is (C$_1$-C$_6$)-alkyl, benzyl, (C$_6$-C$_{10}$)-aryl or tetramethyl-tetrahydronaphthalene;
R3 is H or (C$_1$-C$_6$)-alkyl; or
R2 and R3 together with the nitrogen atom carrying them may form a monocyclic saturated 5- to 6-membered ring system or a bicyclic saturated or partially unsaturated 9- to 10-membered ring system whose individual members of the ring systems may be replaced by one to two atoms or atomic groups from the series —CHR5-, —CR5R5-, —(C=R5)-, —NR5-, —O—, —S—, with the proviso that two units from the series —O—, —S— may not be adjacent;
R4 is hydrogen, (C$_1$-C$_6$)-alkyl or benzyl;
R5 is (C$_1$-C$_6$)-alkyl, halogen, trifluoromethyl, COOR4, cyclopropyl or cyclopropylene.

Particularly preferred compounds of the formula I are further those in which
W is —(C=O)—;
X is =C(—R)— or =N—;

Y is —O—;
R is hydrogen, halogen, nitro, hydroxy or $(C_1-C_6)$-alkyl;
R1 is H or $(C_1-C_6)$-alkyl;
R2 is $(C_1-C_6)$-alkyl, benzyl or $(C_6-C_{10})$-aryl;
R3 is $(C_1-C_6)$-alkyl; or
R2 and R3 together with the nitrogen atom carrying them may form a monocyclic saturated 5- to 6-membered ring system or a bicyclic saturated or partially unsaturated 9- to 10-membered ring system whose individual members of the ring systems may be replaced by an atom or an atomic group from the series —CHR5- or —NR5-; and
R5 is $(C_1-C_6)$-alkyl or cyclopropyl.

Particularly preferred compounds of the formula II are also those in which
W is —(C=O)—;
X is =C(—R)— or =N—;
Y is —O—;
R is hydrogen, halogen, $(C_1-C_6)$-alkyl, hydroxy, amino, COOR4, trifluoromethyl, $(C_1-C_6)$-alkylsulfonyl, nitro, pentafluorosulfanyl, $(C_6-C_{10})$-aryl, CO—NR2R3, O—CO—NR2R3 or O—CO—$(C_1-C_6)$-alkylene-CO—O—$(C_1-C_6)$-alkyl;
R1 is H, $(C_1-C_6)$-alkyl or benzyl;
R2 is $(C_1-C_6)$-alkyl, $(C_6-C_{10})$-aryl or tetramethyl-tetrahydronaphthalene;
R3 is H or $(C_1-C_6)$-alkyl; or
R2 and R3 together with the nitrogen atom carrying them may form a monocyclic saturated 5- to 6-membered ring system or a bicyclic saturated or partially unsaturated 9- to 10-membered ring system whose individual members of the ring systems may be replaced by one to two atoms or atomic groups from the series —CHR5-, —CR5R5-, —(C=R5)-, —NR5-, —O—, —S—, with the proviso that two units from the series —O—, —S— may not be adjacent;
R4 is hydrogen, $(C_1-C_6)$-alkyl or benzyl; and
R5 is $(C_1-C_6)$-alkyl, halogen, trifluoromethyl, COOR4, cyclopropyl or cyclopropylene.

Very particularly preferred compounds of the formula II are those in which
NR2R3 is piperidine which comprises the atomic member CHR5 in position 4.

The invention relates to compounds of the formulae I or II in the form of their salts, racemates, racemic mixtures and pure enantiomers, and to their diastereomers and mixtures thereof.

The alkyl radicals in the substituents R, R1, R2, R3, R4, R5 may be either straight-chain or branched. Halogen is fluorine, chlorine, bromine or iodine, in particular fluorine or chlorine.

Aryl means a monocyclic or bicyclic aromatic hydrocarbon radical of 6 to 10 ring atoms which may is substituted independently with one to four substituents, preferably one or two substituents as described herein.

Heteroaryl means a monocyclic or bicyclic radical of 5 to 12 ring atoms having at least one aromatic ring containing one, two or three ring heteroatoms selected from N, O, or S, the remaining ring atoms being C.

Unless otherwise indicated, the terms used herein are defined as follows:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I or II of the invention, for example an ester, which on administration to a mammal such as, for example, a human is able to form (directly or indirectly) a compound of the formula I or II or an active metabolite thereof.

Physiologically functional derivatives include prodrugs of the compounds of the invention as, for example, described in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I or II" hereinafter refer to compound(s) of the formula I or II as described above, and their salts, solvates and physiologically functional derivatives as described herein.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

Use

The compounds of the invention of the general formulae I or II have a surprising inhibitory effect on hormone sensitive lipase, HSL, an allosteric enzyme in adipocytes which is inhibited by insulin and is responsible for the breakdown of fats in fat cells and thus for transferring fat constituents into the blood stream. Inhibition of this enzyme is therefore equivalent to an insulin-like effect of the compounds of the invention, eventually leading to reduction of free fatty acids in the blood and of blood glucose. They can therefore be employed for metabolic derangements such as, for example, for non-insulin-dependent diabetes mellitus, for diabetic syndrome and for direct pancreatic damage.

Compounds of this type are particularly suitable for the treatment and/or prevention of 1.
- disorders of fatty acid metabolism and glucose utilization disorders
- disorders in which insulin resistance is involved 2. Diabetes mellitus, especially type 2 diabetes, including the prevention of the sequelae associated therewith.
   Particular aspects in this connection are
   - hyperglycemia,
   - improvement in insulin resistance,
   - improvement in glucose tolerance,
   - protection of the pancreatic β cells
   - prevention of macro- and microvascular disorders 3. Dyslipidemias and their sequelae such as, for example, atherosclerosis, coronary heart disease, cerebrovascular disorders etc, especially those (but not restricted thereto) which are characterized by one or more of the following factors:
   - high plasma triglyceride concentrations, high postprandial plasma triglyceride concentrations,
   - low HDL cholesterol concentration
   - low ApoA lipoprotein concentrations
   - high LDL cholesterol concentrations
   - small dense LDL cholesterol particles
   - high ApoB lipoprotein concentrations 4. Various other conditions which may be associated with the metabolic syndrome, such as:
   - obesity (excess weight), including central obesity
   - thromboses, hypercoagulable and prothrombotic states (arterial and venous)
   - high blood pressure
   - heart failure such as, for example (but not restricted thereto), following myocardial infarction, hypertensive heart disease or cardiomyopathy 5. Other disorders or conditions in which inflammatory reactions or cell differentiation may for example be involved are:
   - atherosclerosis such as, for example (but not restricted thereto), coronary sclerosis including angina pectoris or myocardial infarction, stroke
   - vascular restenosis or reocclusion
   - chronic inflammatory bowel diseases such as, for example, Crohn's disease and ulcerative colitis
   - pancreatitis
   - other inflammatory states
   - retinopathy
   - adipose cell tumors
   - lipomatous carcinomas such as, for example, liposarcomas
   - solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   - acute and chronic myeloproliferative disorders and lymphomas
   - angiogenesis
   - neurodegenerative disorders
   - Alzheimer's disease
   - multiple sclerosis
   - Parkinson's disease
   - erythemato-squamous dermatoses such as, for example, psoriasis
   - acne vulgaris
   - other skin disorders and dermatological conditions which are modulated by PPAR
   - eczemas and neurodermatitis
   - dermatitis such as, for example, seborrheic dermatitis or photodermatitis
   - keratitis and keratoses such as, for example, seborrheic keratoses, senile keratoses, actinic keratosis, photo-induced keratoses or keratosis follicularis
   - keloids and keloid prophylaxis
   - warts, including condylomata or condylomata acuminata
   - human papilloma viral (HPV) infections such as, for example, venereal papillomata, viral warts such as, for example, molluscum contagiosum, leukoplakia
   - papular dermatoses such as, for example, lichen planus
   - skin cancer such as, for example, basal-cell carcinomas, melanomas or cutaneous T-cell lymphomas
   - localized benign epidermal tumors such as, for example, keratoderma, epidermal naevi
   - chilblains
   - high blood pressure
   - syndrome X
   - polycystic ovary syndrome (PCOS)
   - asthma
   - osteoarthritis
   - lupus erythematosus (LE) or inflammatory rheumatic disorders such as, for example, rheumatoid arthritis
   - vasculitis
   - wasting (cachexia)
   - gout
   - ischemia/reperfusion syndrome
   - acute respiratory distress syndrome (ARDS)
   - lypodystrophy and lipodystrophic states, also for treating adverse drug effects (e.g. following medicaments for treating HIV or tumours)

Formulations

The amount of a compound of the invention necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I or II may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of the invention. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I or II used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I or II; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I or II with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I or II, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I or II with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single pouches which are suitable for long-term close contact with the patient's epidermis. Such pouches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formulae I and II are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I or II in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I or II are administered in combination with insulin.

In one embodiment of the invention, the compounds of the formula I or II are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I or II are administered in combination with a sulfonylurea such as, for example, tolbutamide, glibenclamide, glipizide or glimepiride.

In one embodiment, the compounds of the formula I or II are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I or II are administered in combination with a biguanide such as, for example, metformin.

In a further embodiment, the compounds of the formula I or II are administered in combination with a meglitinide such as, for example, repaglinide.

In one embodiment, the compounds of the formula I or II are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I or II are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I or II are administered in combination with a PPAR-gamma agonist such as, for example, rosiglitazone, pioglitazone.

In one embodiment, the compounds of the formula I or II are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I or II are administered in combination with an α-glucosidase inhibitor such as, for example, miglitol or acarbose.

In one embodiment, the compounds of the formula I or II are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I or II are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I or II are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I or II are administered in combination with a polymeric bile acid adsorbent such as, for example, cholestyramine, colesevelam.

In one embodiment of the invention, the compounds of the formula I or II are administered in combination with a cholesterol absorption inhibitor as described for example in WO 0250027, or ezetimibe, tiqueside, pamaqueside.

In one embodiment of the invention, the compounds of the formula I or II are administered in combination with an LDL receptor inducer (see, for example, U.S. Pat. No. 6,342,512).

In one embodiment, the compounds of the formula I or II are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Hoechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I or II are administered in combination with a PPARalpha agonist.

In one embodiment of the invention, the compounds of the formula I or II are administered in combination with a mixed PPAR alpha/gamma agonist such as, for example, AZ 242 (Tesaglitazar, (S)-3-(4-[2-(4-methanesulfonyloxyphenyl)ethoxy]-phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I or II are administered in combination with a fibrate such as, for example, fenofibrate, gemfibrozil, clofibrate, bezafibrate.

In one embodiment of the invention, the compounds of the formula I or II are administered in combination with nicotinic acid or niacin.

In one embodiment of the invention, the compounds of the formula I or II are administered in combination with a CETP inhibitor, e.g. CP-529, 414 (torcetrapib).

In one embodiment of the invention, the compounds of the formula I or II are administered in combination with an ACAT inhibitor.

In one embodiment of the invention, the compounds of the formula I or II are administered in combination with an MTP inhibitor such as, for example, implitapide.

In one embodiment of the invention, the compounds of the formula I or II are administered in combination with an antioxidant.

In one embodiment of the invention, the compounds of the formula I or II are administered in combination with a lipoprotein lipase inhibitor.

In one embodiment of the invention, the compounds of the formula I or II are administered in combination with an ATP citrate lyase inhibitor.

In one embodiment of the invention, the compounds of the formula I or II are administered in combination with a squalene synthetase inhibitor.

In one embodiment of the invention, the compounds of the formula I or II are administered in combination with a lipoprotein(a) antagonist.

Antiobesity Agents

In one embodiment of the invention, the compounds of the formula I or II are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I or II are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I or II are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I or II are administered in combination with medicaments having an antiinflammatory effect.

In one embodiment, the compounds of the formula I or II are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds of the invention of the formulae I or II was tested in the following enzyme assay system:

Substrate Preparation:

Preparation of NAG (NBD monoacyl glyceride) substrate:

6 mg of phosphatidylcholine and 6 mg of phosphatidylinositol are each dissolved in 1 ml of chloroform. 10 mg of NAG are dissolved in 1 ml of chloroform. Two parts of phosphatidylinositol solution (e.g. 83.5 µl) and one part of phosphatidylcholine solution (e.g. 41.5 µl) and 100 µl of NAG solution are pipetted together into plastic scintillation vessels (final concentration in the assay: 0.0375 mg of phospholipid/ml; 0.05 mg/NAG/ml). The chloroform (225 µl total volume) is completely removed by passing a stream of N2 over it. The dried substrate can be stored at 4° C. for up to 3 days. To prepare the phospholipid vesicles/micelles with intercalated NAG (on the day of the assay), the dried substrate is taken up in 20 ml of assay buffer (25 mM Tris/HCl, pH 7.4; 150 mM NaCl) and two ultrasound treatments with an ultrasonic probe (Branson Sonifier Type II, standard microtip): 1st treatment setting 2, 2×1 min, in between 1 min on ice each time; 2nd treatment setting 4, 2×1 min, in between 1 min on ice each time. During this procedure, the color of the substrate solution changes from yellow (extinction maximum 481 nm) to red (extinction maximum 550 nm) owing to intercalation of NAG between the phospholipid molecules in the vesicles/micelles. Before use as substrate (within the next 2 h), the solution is incubated on ice for 15 min.

Indirect NAG Assay:

The assay is carried out in 1.5 ml Eppendorf vessels or 96-well plates at 30° C. for 60 min. To find HSL inhibitors, 10 µl of the test substance are introduced into assay buffer (25 mM Tris/HCl, pH 7.4; 150 mM NaCl) in the presence of 16.6% DMSO. 180 µl of the substrate solution (20 µg/ml phosphatidylcholine, 10 µg/ml phosphatidylinositol, 50 µg/ml NAG in assay buffer) are added. After preincubation at 30° C. for 15 min, 20 μl of the enzyme solution in assay buffer (diluted 1- to 4-fold are pipetted in, and the extinction at 480 nm is immediately measured in a cuvette photometer (0.5 ml cuvette) or microtiter plate reader. After incubation at 30° C. for 60 min, the extinction is measured again. The increase in extinction at 480 nm is a measure of the enzymic activity. Under standard conditions, 20 μg of partially purified HSL lead to a change of 0.4=4000 arb. units in extinction.

Direct NAG Assay:

As an alternative to measurement of the change in extinction of the substrate solution, the products of the HSL reaction are investigated by phase separation/thin-layer chromatography. For this purpose, 1.3 ml of methanol/chloroform/heptane (10:9:7) and then 0.4 ml of 0.1 M NaOH are added to the incubation mixture (200 μl total volume, see indirect NAG assay) in 2 ml Eppendorf vessels. After vigorous mixing (10 sec), phase separation is initiated by centrifugation (800×g, 20 min, room temperature). Equivalent volumes (e.g. 0.4 ml) are taken from the aqueous upper phase, and the extinction at 481 nm is determined in a photometer. For thin-layer chromatography, the aqueous phase is dried (SpeedVac) and then taken up in 50 μl of tetrahydrofuran. 5 μl samples are loaded onto silica gel Si-60 plates (Merck). The chromatography is carried out with 78 ml of diethyl ether/22 ml of petroleum ether/1 ml of glacial acetic acid as mobile phase. The amount of liberated fluorescent NBD-fatty acid is determined by Phosphorimaging (Molecular Dynamics, Storm 840 and ImageQuant Software) at an excitation wavelength of 460 nm and emission wavelength of 540-560 nm.

Enzyme Preparation:

Preparation of the partially purified HSL:

Isolated rat fat cells are obtained from epididymal adipose tissue from untreated male rats (Wistar, 220-250 g) by collagenase treatment in accordance with published methods (e.g. S. Nilsson et al., Anal. Biochem. 158, 1986, 399-407; G. Fredrikson et al., J. Biol. Chem. 256, 1981, 6311-6320; H. Tornquist et al., J. Biol. Chem. 251, 1976, 813-819). The fat cells from 10 rats are washed three times by flotation with 50 ml of homogenization buffer (25 ml Tris/HCl, pH 7.4, 0.25 M sucrose, 1 mM ETDA, 1 mM DTT, 10 μg/ml leupeptin, 10 μg/ml antipain, 20 μg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.) and suspended in 2.5 ml of 20 mM Tris/HCl, pH 7.0, 1 mM EDTA, 65 mM NaCl, 13% sucrose, 1 mM DTT, 10 μg/ml leupeptin/pepstatin/antipain. The suspension is dialyzed against 25 mM Tris/HCl, pH 7.4, 50% glycerol, 1 mM DTT, 10 μg/ml leupeptin, pepstatin, antipain at 4° C. overnight and then loaded onto a hydroxiapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at −70° C. for 4 to 6 weeks.

Assay:

To prepare the substrate, 25-50 μCi of [3H]trioleoylglycerol (in toluene), 6.8 μmol of unlabeled trioleoylglycerol and 0.6 mg of phospholipids (phosphatidylcholine/phosphatidylinositol 3:1 w/v) are mixed, dried with N2 and then taken up in 2 ml of 0.1 M KPi (pH 7.0) by ultrasound treatment (Branson 250, microtip, setting 1-2, 2×1 min with an interval of 1 min). After addition of 1 ml of KPi and renewed ultrasound treatment (4×30 sec on ice with intervals of 30 sec), 1 ml of 20% BSA (in KPi) is added (final concentration of trioleoylglycerol 1.7 mM). For the reaction, 100 μl of substrate solution are pipetted into 100 μl of HSL solution (HSL prepared as above, diluted in 20 mM KPi, pH 7.0, 1 mM EDTA, 1 mM DTT, 0.02% BSA, 20 μg/ml pepstatin, 10 μg/ml leupeptin) and incubated at 37° C. for 30 min. Addition of 3.25 ml of methanol/chloroform/heptane (10:9:7) and of 1.05 ml of 0.1 M K2CO3, 0.1 M boric acid (pH 10.5) is followed by thorough mixing and finally centrifugation (800×g, 20 min). After phase separation, one equivalent of the upper phase (1 ml) is removed and the radioactivity is determined by liquid scintillation measurement.

Evaluation:

Substances are normally tested in four independent mixtures. The inhibition of the HSL enzymatic activity by a test substance is determined by comparing with an uninhibited control reaction. The IC50 is calculated from an inhibition plot with min. 10 concentrations of the test substance. The GRAPHIT, Elsevier-BIOSOFT software package is used to analyze the data.

The compounds of the claimed invention showed inhibitions in the $IC_{50}$ range 1 nM-1 μM in this assay.

The compounds of the invention of the general formulae I or II are prepared by methods known per se, e.g. by acylation of substituted or unsubstituted indazoles III with carbamoyl chlorides IV (method A), or in two stages by reacting indazoles III with phosgene or equivalents such as trichloromethyl chlorocarbonate or ditrichloromethyl carbonate and further reaction of the resulting indazolecarbonyl chloride with amines or anilines (method B). For compounds in which R3 is hydrogen, the indazoles III can also be reacted with the appropriate isocyanates R2-N=C=O.

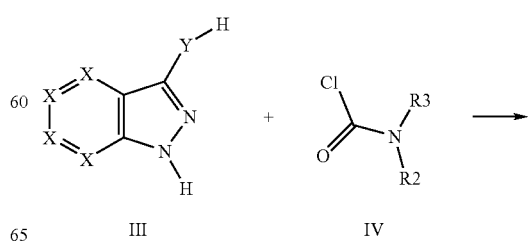

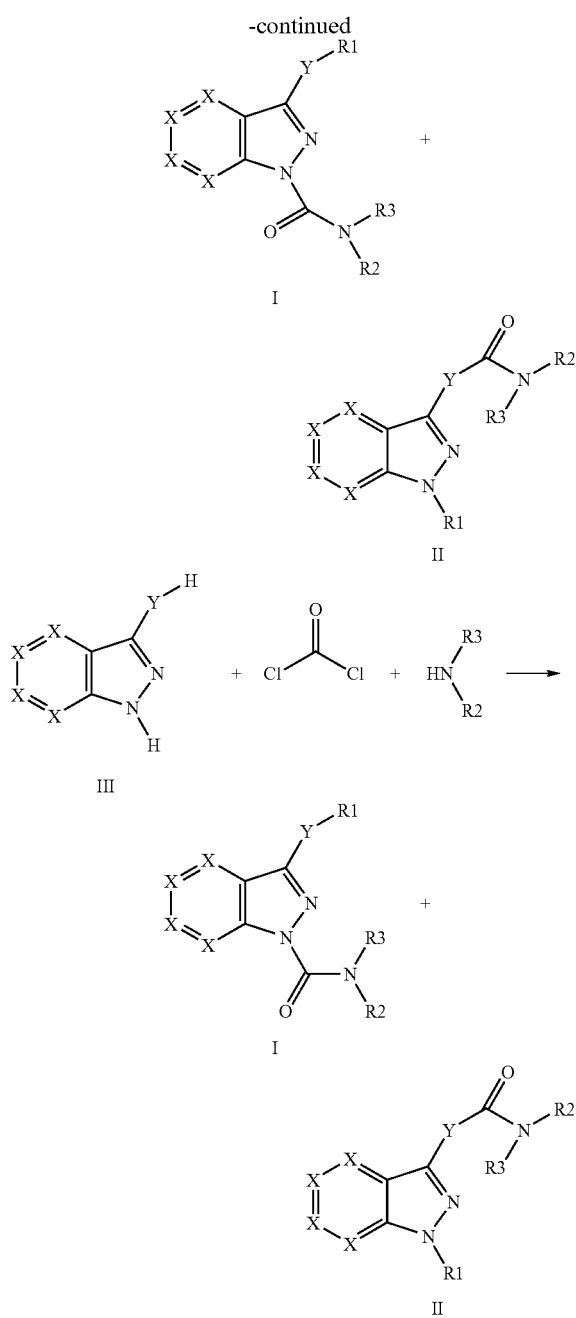

Since acids are usually liberated in these reactions, it is advisable to add bases such as pyridine, triethylamine, sodium hydroxide solution or alkali metal carbonates for expedition. The reactions can be carried out in wide temperature ranges. It has usually proved to be advantageous to operate at from 0° C. to the boiling point of the solvent used. Examples of solvents employed are methylene chloride, THF, DMF, toluene, ethyl acetate, n-heptane, dioxane, diethyl ether or pyridine. If anhydrous conditions are used, strong bases such as lithium hydride, sodium hydride or potassium tert-butoxide in aprotic solvents such as THF or DMF have also proved suitable.

The indazoles employed as starting compounds III, or corresponding aza-substituted derivatives, are commercially available or can be prepared by processes known from the literature (e.g. L. Baiocchi, G. Corsi Synthesis (1978), 633-648, I. Sekikawa et al. J. Het. Chem. (1973), 931-932).

The compounds of the general formulae I and II are separated and purified by chromatographic methods known per se.

The examples detailed below serve to illustrate the invention without, however, restricting it.

EXAMPLES

Example 1

1H-Indazol-3-yl 4-methylpiperidine-1-carboxylate 300 mg (2.24 mmol) of 1H-indazol-3-ol were dissolved in 25 ml of THF and cooled to −20° C.: 1.3 ml (2.46 mmol) of phosgene in toluene (20 percent) were added dropwise and the reaction mixture was stirred for 90 min, during which it warmed to room temperature. The reaction mixture was concentrated and evacuated once again with a few ml of toluene. The residue was dissolved in 15 ml of THF, 265 μl (2.2 mmol) of 4-methylpiperidine were added dropwise and the mixture was stirred at room temperature for 3 h, concentrated and purified by preparative HPLC (PR18, acetonitrile/water 0.1% TFA). Yield: 347 mg (60%), M+H+: 260.4.

Example 2

4-Methylpiperidine-1-carbonyl chloride 9 g (90.75 mmol) of 4-methylpiperidine and 13.9 ml (100 mol) of triethylamine were dissolved in 100 ml of THC and, at −30° C., 54.9 ml (100 mmol) of phosgene in toluene (20 percent) were added, and the mixture was stirred for 2.5 h, during which it warmed to room temperature. The reaction mixture was concentrated, the residue was mixed with methylene chloride and filtered off, and the filtrate was concentrated. The crude product (12.7 g) was reacted without further purification.

Example 3

4-Fluoro-1H-indazol-3-yl 4-methylpiperidine-1-carboxylate 100 mg (0.66 mmol) of 4-fluoro-1H-indazol-3-ol and 116.8 mg (0.72 mmol) of 4-methylpiperidine-1-carbonyl chloride (Example 2) in 10 ml of pyridine were heated under reflux for 4 h and left to stand overnight. Addition of 24 mg of 4-methyl-piperidine-1-carbonyl chloride was followed by heating under reflux for a further 2 h while the pyridine was distilled off in vacuo, and the residue was dissolved in water and extracted with ethyl acetate. The organic phase was concentrated and purified by preparative HPLC (PR18, acetonitrile/water 0.1% TFA). Yield: 56 mg (31%), M+H+: 278.1.

Example 4

1-Methyl-1H-indazolyl-3-yl 4-methylpiperidine-1-carboxylate 80.1 mg (0.31 mmol) of 1H-indazol-3-yl 4-methylpiperidine-1-carboxylate (Example 1), 38.1 mg (0.34 mmol) of potassium-tert-butoxide and 48.2 mg (0.34 mmol) of iodomethane were stirred at room temperature for 48 h. The solvent was distilled off in vacuo, and the residue was dissolved in water and extracted with ethyl acetate. The organic phase was concentrated and purified by preparative HPLC (PR18, acetonitrile/water 0.1% TFA). Yield: 7 mg (8%), M+H+: 274.1.

Example 5

100 mg (0.56 mmol) of 6-nitro-1H-indazol-3-ol and 135.3 mg (0.83 mmol) of 4-methylpiperidine-1-carbonyl chloride (Example 2) in 10 ml of pyridine were heated under reflux for 5 h and left to stand overnight. Pyridine was distilled off in vacuo, and the residue was dissolved in water and extracted with ethyl acetate. The organic phase was concentrated and purified by preparative HPLC (PR18, acetonitrile/water 0.1% TFA). Yield: 5 mg (3%) of A: (3-hydroxy-6-nitroindazol-1-yl)-(4-methyl-piperidin-1-yl)methanone, M+H+: 305.1 and 64 mg (38%) of B: 6-nitro-1H-indazol-3-yl 4-methylpiperidine-1-carboxylate, M+H+: 305.1.

Example 6

5-Nitro-1H-indazol-3-yl 4-methylpiperidine-1-carboxylate 200 mg (1.12 mmol) of 5-nitro-1H-indazol-3-ol and 180.4 mg (1.67 mmol) of 4-methylpiperidine-1-carbonyl chloride (Example 2) in 20 ml of pyridin were heated under reflux for 5 h and left to stand overnight. Pyridine was distilled off in vacuo, and the residue was dissolved in water and extracted with ethyl acetate. The organic phase was concentrated and purified by preparative HPLC (PR18, acetonitrile/water 0.1% TFA). Yield: 48 mg (14%), M+H+: 304.99.

Example 7

6-Amino-1H-indazol-3-yl 4-methylpiperidine-1-carboxylate 30 mg (0.1 mmol) of 6-nitro-1H-indazol-3-yl 4-methylpiperidine-1-carboxylate (Example 5B) in 15 ml of ethanol were hydrogenated in the presence of 10% palladium/carbon under a hydrogen pressure of 2 bar at room temperature for 2.5 h. The catalyst was filtered off with suction, and the filtrate was concentrated. Yield: 21 mg (76%), M+H+: 275.2.

Example 8

Example 1 was repeated with 2 g (14.9 mmol) of 1H-indazol-3-ol. In this case it was possible to isolate A: 1H-indazol-3-yl 4-methylpiperidine-1-carboxylate also the isomeric products B: (3-hydroxyindazol-1-yl)-(4-methylpiperidin-1-yl)methanone and C: 2-(4-methylpiperidine-1-carbonyl)-1,2-dihydroindazol-3-one.

Example 9

1H-Pyrazolo[3,4-b]pyridin-3-yl 4-methyl piperidine-1-carboxylate a) 1H-Pyrazolo[3,4-b]pyridin-3-ol: 5 g (26.94 mmol) of ethyl 2-chloronicotinate and 4.76 g (80.82 mmol) of hydrazine hydrate (85 percent) in 10 ml of ethanol were heated under reflux for 6 h. The reaction mixture was concentrated. Yield: 3.5g (96%), M+H+: 135.9.

b) 300 mg (2.2 mmol) of 1H-pyrazolo[3,4-b]pyridin-3-ol and 538.2 mg (3.3 mmol) of 4-methylpiperidine-1-carbonyl chloride (Example 2) in 25 ml of pyridine were heated under reflux for 4 h and left to stand overnight. Addition of 24 mg of 4-methylpiperidine-1-carbonyl chloride were followed by further heating under reflux for 2 h, the pyridine was distilled off in vacuo, and the residue was dissolved in water and extracted with ethyl acetate. The organic phase was concentrated and purified by preparative HPLC (PR18, acetonitrile/water 0.1% TFA). Yield: 99 mg (17%), M+H+: 261.28.

Example 10

500 mg (2.16 mmol) of 1H-indazol-3-ylamine; compound with sulfuric acid and 419.3 mg (2.59 mmol) of 4-methylpiperidine-1-carbonyl chloride (Example 2) and 300 µl (4.32 mmol) of triethylamine in 30 ml of pyridine were heated under reflux for 5 h and left to stand overnight. Addition of 302 µl of triethylamine and and 390 mg of 4-methylpiperidine-1-carbonyl chloride was followed by heating for a further 2.5 h. Pyridine was distilled off in vacuo, and the residue was dissolved in water and extracted with ethyl acetate. The organic phase was concentrated and purified by preparative HPLC (PR18, acetonitrile/water 0.1% TFA). Yield: 55 mg (10%) of A: 4-methylpiperidine-1-carboxylic acid (1H-indazol-3-yl)amide, M+H+: 259.1 and 36.4 mg (7%) of B: (3-aminoindazol-1-yl)-(4-methylpiperidin-1-yl)methanone, M+H+: 259.1.

Example 11

4-Trifluoromethylpiperidine-1-carbonyl chloride

Carbonic acid ditrichloromethyl ester (840 mg, 2.83 mmol) were dissolved in 30 ml of methylene chloride and, in an ice bath, 2.06 ml (25.24 mmol) of pyridine were slowly added. After 30 min, 4-trifluoromethylpiperidine hydrochloride (1.45 g, 7.65 mmol) was slowly added in portions. After removal of the ice bath, stirring was continued for 90 min, the precipitate was filtered off and washed with n-heptane, and the filtrate was concentrated. The resulting product (1.9 g) still contains some salt and was reacted further directly.

Example 12

4-Trifluoromethylpiperidine-1-carboxylic acid 6-hydroxy-4-methyl-1H-pyrazolo-[3,4-b]pyridin-3-yl ester 4-Methyl-1H-pyrazolo[3,4-b]pyridine-3,6-diol (1 g, 6.05 mmol), 4-trifluoromethyl-piperidine-1-carbonyl chloride (1.436 g, 6.6 mmol) and triethylamine (1.68 ml, 12.11 mmol) were stirred in 25 ml of pyridine at room temp for 1 h. Addition of 0.5 ml of triethylamine was followed by stirring for 2 h, concentration and addition of ethyl acetate and water. The resulting precipitate was filtered off with suction and dried. Yield: 765 mg (37%) of 4-trifluoromethylpiperidine-1-carboxylic acid 6-hydroxy-4-methyl-1H-pyrazolo[3,4-b]pyridin-3-yl ester. The organic phase was separated off, concentrated and purified by preparative HPLC (PR18, acetonitrile/water 0.1% TFA). Yield: 96 mg (5%) of 4-trifluoromethylpiperidine-1-carboxylic acid 6-hydroxy-4-methyl-1H-pyrazolo[3,4-b]pyridin-3-yl ester. M+H+: 345.13; 102 mg (3%) of 4-trifluoromethylpiperidine-1-carboxylic acid 4-methyl-3-(4-trifluoromethylpiperidine-1-carbonyloxy)-1H-pyrazolo[3,4-b]pyridin-6-yl ester, M+H+: 524.20; 106 mg (3%) of 4-trifluoromethylpiperidine-1-carboxylic acid 6-hydroxy-4-methyl-1-(4-trifluoromethylpiperidine-1-carbonyl)-1H-pyrazolo[3,4-b]pyridin-3-yl ester, M+H+: 524.52; 54 mg (1.3%) of 4-trifluoromethylpiperidine-1-carboxylic acid 4-methyl-3-(4-trifluoromethylpiperidine-1-carbonyloxy)-1-(4-trifluoromethylpiperidine-1-carbonyl)-1H-pyrazolo[3,4-b]pyridin-6-yl ester, M+H+: 703.36.

Example 13

4-Methylpiperazine-1-carboxylic acid 4-methyl-3-(4-trifluoromethylpiperidine-1-carbonyloxy)-1H-pyrazolo[3,4-b]pyridin-6-yl ester; compound with trifluoroacetic acid 4-Trifluoromethylpiperidine-1-carboxylic acid 6-hydroxy-4-methyl-1H-pyrazolo-[3,4-b]pyridin-3-yl ester (300 mg, 0.87 mmol), 4-methylpiperazine-1-carbonyl chloride hydrochloride (191 mg, 0.96 mmol) and triethylamine (0.48 ml, 3.48 mmol) were stirred in 10 ml of pyridine at room temp. for 5 h. Addition of 0.4 ml of triethylamine and 100 mg of 4-methylpiperazine-1-carbonyl chloride hydrochloride was followed by stirring for 1 h, concentration and addition of ethyl acetate and water and adjustment to pH 8. The organic phase was separated off (multiple extraction), concentrated and purified by preparative HPLC (PR18, acetonitrile/water 0.1% TFA). Yield: 125 mg (25%) of 4-methylpiperazine-1-carboxylic acid 4-methyl-3-(4-trifluoromethyl-piperidine-1-carbonyloxy)-1H-pyrazolo[3,4-b]pyridin-6-yl ester; compound with trifluoroacetic acid, M+H+: 471.24; 82 mg (13%) 4-trifluoromethylpiperidine-1-carboxylic acid 6-hydroxy-4-methyl-1-(4-methylpiperazine-1-carbonyl)-1H-pyrazolo[3,4-b]pyridin-3-yl ester; compound with trifluoroacetic acid, M+H+: 471.27.

Example 14

6-Nitro-1H-indazol-3-ol

2-Fluoro-4-nitrobenzoic acid methyl ester (5 g, 25.11 mmol) and hydrazine hydrate (1.34 ml, 27.62 mmol) were dissolved in 250 ml of ethanol and heated under reflux for 11 h. A further 0.26 ml of hydrazine hydrate were added and heated under reflux for a further 6 h, and the mixture was concentrated and ethyl acetate and water were added. The precipitated residue was filtered off with suction and dried. Purification by preparative HPLC (PR18, acetonitrile/water 0.1% TFA) resulted in 1.39 g of product, M+H+: 180.05.

Example 15

6-Fluoro-1H-indazol-3-ol

2-Amino-4-fluorobenzoic acid (25 g, 161.2 mmol) were suspended in 250 ml of water and 39 ml of conc. hydrochloric acid. At 0° C., sodium nitrite (11.2 g, 161.2 mmol) in 30 ml of water were added dropwise at below 10° C. After 30 min at room temp., sodium sulfite (69 g, 400 mmol) in 250 ml of water were added. After stirring for 2 h, 30 ml of conc. hydrochloric acid were added, and the mixture was left to stand overnight. It was then heated under reflux for 9 h, cooled and adjusted to pH 5.5 with sodium bicarbonate. The precipitate was filtered off with suction and dried.

Yield: 19.8 g, (81%), M+H+: 152.94.

Example 16

3-Hydroxy-1H-indazole-6-carboxylic acid

2-Aminoterephthalic acid dimethyl ester (5 g, 23.9 mmol) were dissolved in 40 ml of water and 6 ml of conc. hydrochloric acid. At 0° C., sodium nitrite (1.65 g, 23.9 mmol) in 5 ml of water were added dropwise at below 10° C. After 30 min at room temp., sodium sulfite (11.02 g, 87.42 mmol) in 40 ml of water were added. After stirring for 1 h, 10 ml of conc. hydrochloric acid were added, and the mixture was left to stand overnight. It was then heated at 80° C. for 24 h, cooled and adjusted to pH 5.5 with sodium hydroxide solution. The precipitate was filtered off with suction and dried.

Yield: 2.29 g, (54%), M+H+: 179.04.

Example 17

3-Hydroxy-4-methyl-1H-pyrazolo[3,4-b]pyridine-6-carboxylic acid

5-Amino-2H-pyrazol-3-ol (3.1 g, 31.6 mmol) were suspended in 100 ml of methanol. Then sodium methoxide (5.1 g, 95 mmol) and 2,4-dioxopentanoic acid ethyl ester (5 g, 31.6 mmol) were added, and the mixture was heated up under reflux for 12 h. The solvent was removed in a rotary evaporator, water was added to the residue, the precipitate was filtered off with suction, and the filtrate was adjusted to pH 6 with dilute hydrochloric acid. The precipitated product (both precipitates) was filtered off with suction and dried. Yield: 4.9 g (70%), M+H+: 194.09.

The following compounds were prepared in analogy to the described examples:

| Example | Name | M+H+ |
|---|---|---|
| 18 | 3-Methylpiperidine-1-carboxylic acid 1H-indazol-3-yl ester | 260.2 |
| 19 | (3,4-Dihydro-2H-quinolin-1-yl)-(3-hydroxy-indazol-1-yl)-methanone | 294.3 |
| 20 | (3-Hydroxy-indazol-1-yl)-pyrrolidin-1-yl-methanone | 232.3 |
| 21 | (3-Hydroxy-indazol-1-yl)-thiomorpholin-4-yl-methanone | 264.4 |
| 22 | (3,4-Dihydro-1H-isoquinolin-2-yl)-(3-hydroxy-indazol-1-yl)-methanone | 294.5 |
| 23 | 3-Hydroxy-indazole-1-carboxylic acid methyl-phenyl-amide | 268.3 |
| 24 | 3-Methyl-piperidine-1-carboxylic acid 1-methyl-1H-indazol-3-yl ester | 274.4 |
| 25 | (3-Methoxy-indazol-1-yl)-(3-methyl-piperidin-1-yl)-methanone | 274.4 |
| 26 | 3-Hydroxy-indazole-1-carboxylic acid dibutylamide | 290.16 |
| 27 | Diethyl-carbamic acid 1H-indazol-3-yl ester | 234.11 |
| 28 | Diisopropyl-carbamic acid 1H-indazol-3-yl ester | 262.13 |
| 29 | Piperidine-1-carboxylic acid 1H-indazol-3-yl ester | 246.10 |
| 30 | (1,3-Dihydro-isoindol-2-yl)-(3-hydroxy-indazol-1-yl)-methanone | 280.12 |
| 31 | 4-Methyl-piperidine-1-carboxylic acid 6-trifluoromethyl-1H-indazol-3-yl ester | 328.16 |
| 32 | 4-Methyl-piperidine-1-carboxylic acid 6-fluoro-1H-indazol-3-yl ester | 278.13 |
| 33 | 4-Methyl-piperidine-1-carboxylic acid 6-chloro-1H-indazol-3-yl ester | 294.06 |
| 34 | 4-Methyl-piperidine-1-carboxylic acid 6-methyl-1H-indazol-3-yl ester | 274.12 |
| 35 | (6-Chloro-3-hydroxy-indazol-1-yl)-(4-methyl-piperidin-1-yl)-methanone | 294.12 |
| 36 | (3-Hydroxy-indazol-1-yl)-(octahydro-isoindol-2-yl)-methanone | 286.16 |
| 37 | Octahydro-isoindole-2-carboxylic acid 1H-indazol-3-yl ester | 286.17 |
| 38 | 3,4-Dihydro-1H-isoquinoline-2-carboxylic acid 1H-indazol-3-yl ester | 294.13 |
| 39 | 4-Methyl-piperidine-1-carboxylic acid 6-chloro-4-methyl-1H-pyrazolo[3,4-b]pyridin-3-yl ester | 309.14 |
| 40 | (3-Hydroxy-pyrazolo[3,4-b]pyridin-1-yl)-(4-methyl-piperidin-1-yl)-methanone | 261.17 |

| Example | Name | M+H+ |
|---|---|---|
| 41 | 4-Methyl-piperidine-1-carboxylic acid 4-methyl-3-(4-methyl-piperidine-1-carbonyloxy)-1H-pyrazolo[3,4-b]pyridin-6-yl ester | 416.24 |
| 42 | 4-Methyl-piperidine-1-carboxylic acid 6-hydroxy-4-methyl-1H-pyrazolo[3,4-b]pyridin-3-yl ester | 291.20 |
| 43 | (6-Fluoro-3-hydroxy-indazol-1-yl)-(4-methyl-piperidin-1-yl)-methanone | 278.18 |
| 44 | (6-Fluoro-3-hydroxy-indazol-1-yl)-(octahydro-isoindol-2-yl)-methanone | 304.20 |
| 45 | (3,4-Dihydro-1H-isoquinolin-2-yl)-(6-fluoro-3-hydroxy-indazol-1-yl)-methanone | 312.17 |
| 46 | Octahydro-isoindole-2-carboxylic acid 6-fluoro-1H-indazol-3-yl ester | 304.21 |
| 47 | Piperidine-1-carboxylic acid 6-fluoro-1H-indazol-3-yl ester | 264.17 |
| 48 | Methyl-phenyl-carbamic acid 6-fluoro-1H-indazol-3-yl ester | 286.17 |
| 49 | 3,4-Dihydro-1H-isoquinoline-2-carboxylic acid 6-fluoro-1H-indazol-3-yl ester | 312.13 |
| 50 | 4-Methyl-piperidine-1-carboxylic acid 1H-pyrazolo[4,3-c]pyridin-3-yl ester | 261.15 |
| 51 | 4-Methyl-piperidine-1-carboxylic acid 6-bromo-1H-indazol-3-yl ester | 338.08 |
| 52 | 3-(4-Methyl-piperidine-1-carbonyloxy)-1H-indazole-6-carboxylic acid methyl ester | 318.17 |
| 53 | (5,5,8,8-Tetramethyl-5,6,7,8-tetrahydro-naphthalen-2-yl)-carbamic acid 1H-indazol-3-yl ester | 364.8 |
| 54 | 3,4-Dihydro-1H-isoquinoline-2-carboxylic acid 6-chloro-4-methyl-1H-pyrazolo[3,4-b]pyridin-3-yl ester | 343.16 |
| 55 | 4-Methyl-piperidine-1-carboxylic acid 6-trifluoromethyl-1H-pyrazolo[3,4-b]pyridin-3-yl ester | 329.19 |
| 56 | (6-Fluoro-3-methoxy-indazol-1-yl)-(4-methyl-piperidin-1-yl)-methanone | 292.20 |
| 57 | 4-Methyl-piperidine-1-carboxylic acid 5,6-difluoro-1H-indazol-3-yl ester | 296.25 |
| 58 | (3,4-Dihydro-1H-phthalazin-2-yl)-(6-fluoro-3-hydroxy-indazol-1-yl)-methanone | 313.15 |
| 59 | (6-Chloro-3-hydroxy-4-methyl-pyrazolo[3,4-b]pyridin-1-yl)-(3,4-dihydro-1H-isoquinolin-2-yl)-methanone | 343.12 |
| 60 | 4-Methyl-piperidine-1-carboxylic acid 1-benzyl-6-hydroxy-4-methyl-1H-pyrazolo[3,4-b]pyridin-3-yl ester | 381.27 |
| 61 | 4-Methyl-piperidine-1-carboxylic acid 6-methanesulfonyl-1H-indazol-3-yl ester | 338.17 |
| 62 | 4-Methyl-piperidine-1-carboxylic acid 6-hydroxy-1H-pyrazolo[3,4-b]pyridin-3-yl ester | 277.15 |
| 63 | (3,6-Dihydroxy-pyrazolo[3,4-b]pyridin-1-yl)-(4-methyl-piperidin-1-yl)-methanone | 277.15 |
| 64 | (6-Chloro-3-hydroxy-4-methyl-pyrazolo[3,4-b]pyridin-1-yl)-(4-methyl-piperidin-1-yl)-methanone | 309.13 |
| 65 | Succinic acid methyl ester 4-methyl-3-(4-methyl-piperidine-1-carbonyloxy)-1H-pyrazolo[3,4-b]pyridin-6-yl ester | 405.26 |
| 66 | 4-Methyl-piperazine-1-carboxylic acid 6-fluoro-1H-indazol-3-yl ester; compound with trifluoro-acetic acid | 279.15 |
| 67 | 3,4-Dihydro-1H-isoquinoline-2-carboxylic acid 1H-pyrazolo[3,4-b]pyridin-3-yl ester | 295.18 |
| 68 | 4,4-Difluoro-piperidine-1-carboxylic acid 6-fluoro-1H-indazol-3-yl ester | 300.25 |
| 69 | 4,4-Difluor-piperidine-1-carboxylic acid 4-methyl-3-(4-methyl-piperidine-1-carbonyloxy)-1H-pyrazolo[3,4-b]pyridin-6-yl ester | 438.31 |
| 70 | 6,7-Dihydro-4H-thieno[3,2-c]pyridine-5-carboxylic acid 6-fluoro-1H-indazol-3-yl ester | 318.11 |
| 71 | Piperidine-1,4-dicarboxylic acid 4-benzyl ester 1-(6-fluoro-1H-indazol-3-yl)ester | 398.26 |
| 72 | Thiomorpholine-4-carboxylic acid 6-fluoro-1H-indazol-3-yl ester | 282.13 |
| 73 | 4-Trifluoromethyl-piperidine-1-carboxylic acid 6-fluoro-1H-indazol-3-yl ester | 332.16 |
| 74 | 2,6-Dimethyl-morpholine-4-carboxylic acid 6-fluoro-1H-indazol-3-yl ester | 294.18 |
| 75 | 4-Phenyl-piperazine-1-carboxylic acid 6-fluoro-1H-indazol-3-yl ester | 341.21 |
| 76 | Morpholine-4-carboxylic acid 6-fluoro-1H-indazol-3-yl ester | 266.15 |
| 77 | 3,4-Dihydro-1H-phthalazine-2-carboxylic acid 6-fluoro-1H-indazol-3-yl ester; compound with trifluoro-acetic acid | 313.14 |
| 78 | 4,4-Difluoro-piperidine-1-carboxylic acid 6-hydroxy-4-methyl-1H-pyrazolo[3,4-b]pyridin-3-yl ester | 313.17 |
| 79 | 4,4-Difluoro-piperidine-1-carboxylic acid 6-chloro-4-methyl-1H-pyrazolo[3,4-b]pyridin-3-yl ester | 331.14 |
| 80 | 4-Methyl-piperidine-1-carboxylic acid 4,6-difluoro-1H-indazol-3-yl ester | 296.17 |
| 81 | Piperidine-1,4-dicarboxylic acid mono-(6-fluoro-1H-indazol-3-yl)ester | 308.20 |
| 82 | 4-Fluoro-piperidine-1-carboxylic acid 6-fluoro-1H-indazol-3-yl ester | 282.10 |
| 83 | 4-Cyclopropyl-piperazine-1-carboxylic acid 6-fluoro-1H-indazol-3-yl ester | 305.24 |
| 84 | Piperazine-1,4-dicarboxylic acid benzyl ester 6-fluoro-1H-indazol-3-yl ester | 399.13 |
| 85 | 4-Fluoro-piperidine-1,4-dicarboxylic acid 4-ethyl ester 1-(6-fluoro-1H-indazol-3-yl)ester | 354.13 |
| 86 | (4-Cyclopropyl-piperazin-1-yl)-(6-fluoro-3-hydroxy-indazol-1-yl)-methanone | 305.35 |
| 87 | 4,4-Dimethyl-piperidine-1-carboxylic acid 6-fluoro-1H-indazol-3-yl ester | 292.19 |
| 88 | 4-Methyl-piperidine-1-carboxylic acid 6-fluoro-1-methyl-1H-indazol-3-yl ester | 292.13 |
| 89 | 4-(3,4-Dimethyl-phenyl)-piperazine-1-carboxylic acid 1H-indazol-3-yl ester | 351.17 |
| 90 | 4-Trifluoromethyl-piperidine-1-carboxylic acid 6-chloro-4-methyl-1H-pyrazolo[3,4-b]pyridin-3-yl ester | 263.07 |
| 91 | 4-Methyl-piperidine-1-carboxylic acid 5-fluoro-1H-indazol-3-yl ester | 278.22 |
| 92 | 4-Trifluoromethyl-piperidine-1-carboxylic acid 4-methyl-3-(4-methyl-piperidine-1-carbonyloxy)-1H-pyrazolo[3,4-b]pyridin-6-yl ester | 470.18 |
| 93 | 4-Cyclopropylidene-piperidine-1-carboxylic acid 6-fluoro-1H-indazol-3-yl ester | 302.14 |
| 94 | 4-Cyclopropyl-piperazine-1-carboxylic acid 6-hydroxy-4-methyl-1H-pyrazolo[3,4-b]pyridin-3-yl ester | 318.21 |
| 95 | Piperidine-1,4-dicarboxylic acid 4-benzyl ester 1-[4-methyl-3-(4-methyl-piperidine-1-carbonyloxy)-1H-pyrazolo[3,4-b]pyridin-6-yl] ester | 536.40 |
| 96 | 3-Methyl-piperidine-1-carboxylic acid 6-pentafluorosulfanyl 1H-indazol-3-yl ester | 386.32 |
| 97 | 4-Methyl-3-(4-methyl-piperidine-1-carbonyloxy)-1H-pyrazolo[3,4-b]pyridine-6-carboxylic acid | 319.17 |
| 98 | 4-Methyl-piperidine-1-carboxylic acid 4-methyl-6-(4-methyl-piperidine-1-carbonyl)-1H-pyrazolo[3,4-b]pyridin-3-yl ester | 400.26 |
| 99 | 4-Methyl-piperidine-1-carboxylic acid 4-methyl-6-phenyl-1H-pyrazolo[3,4-b]pyridin-3-yl ester | 351.34 |
| 100 | 4-Trifluoromethyl-piperidine-1-carboxylic acid 4,6-difluoro-1H-indazol-3-yl ester | 350.11 |
| 101 | 4-Methyl-piperidine-1-carboxylic acid 6-(4-methyl-piperidine-1-carbonyl)-1H-indazol-3-yl ester | 385.25 |
| 102 | 6-Chloro-3-hydroxy-indazole-1-carboxylic acid benzylamide | 302.10 |
| 103 | 6-Chloro-3-hydroxy-indazole-1-carboxylic acid hexylamide | 296.16 |

What is claimed is:

1. An indazole derivative of the formula II

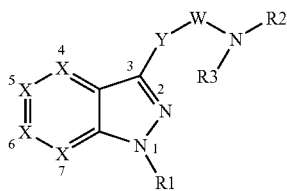

in which the meanings are:

W is —(C=O);
X is C—R;
Y is —O—;
R is hydrogen, halogen, $(C_1-C_6)$-alkyl, $(C_1-C_3)$-alkyloxy-$(C_1-C_3)$-alkylene, hydroxy, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, COOR4, cyano, trifluoromethyl, $(C_1-C_6)$-alkylsulfonyl, $(C_1-C_6)$-alkylsulfinyl, aminosulfonyl, nitro, pentafluorosulfanyl, $(C_6-C_{10})$-aryl, CO—NR2R3, O—CO—NR2R3, O—CO—$(C_1-C_6)$-alkylene-CO—O—$(C_1-C_6)$-alkyl, O—CO—$(C_1-C_6)$-alkylene-CO—OH, O—CO—$(C_1-C_6)$-alkylene-CO—NR2R3 or unsubstituted or mono- or poly- F-substituted $(C_1-C_6)$-alkyloxy;
R1 is H, $(C_1-C_6)$-alkyl or benzyl;
R2 and R3 together with the nitrogen atom carrying them form piperidine which optionally comprises the atomic member CHR5 in position 4;
R4 is hydrogen, $(C_1-C_6)$-alkyl or benzyl;
R5 is $(C_1-C_6)$-alkyl, halogen, trifluoromethyl, or cyclopropylene;

and the physiologically tolerated salts thereof as well as its tautomeric forms.

2. The indazole derivative of claim 1, wherein
X in position 4, 5 and 7 is C—R with R=hydrogen.

3. The indazole derivative of claim 1, wherein
W is —(C=O)—;
X is C—R;
Y is —O—;
R is hydrogen, halogen, $(C_1-C_6)$-alkyl, hydroxy, amino, COOR4, trifluoromethyl, $(C_1-C_6)$-alkylsulfonyl, nitro, pentafluorosulfanyl, $(C_6-C_{10})$-aryl, CO—NR2R3, O—CO—NR2R3 or O—CO—$(C_1-C_6)$-alkylene-CO—O—$(C_1-C_6)$-alkyl;
R1 is H, $(C_1-C_6)$-alkyl or benzyl;
R2 and R3 together with the nitrogen atom carrying them form piperidine which optionally comprises the atomic member CHR5 in position 4;
R4 is hydrogen, $(C_1-C_6)$-alkyl or benzyl; and
R5 is $(C_1-C_6)$-alkyl, halogen, trifluoromethyl or cyclopropylene.

4. The indazole derivative of claim 1, wherein
NR2R3 is piperidine which comprises the atomic member CHR5 in position 4.

5. A pharmaceutical composition comprising one or more of the indazole derivatives of claim 1 and a pharmaceutically acceptable carrier.

* * * * *

UNITED STATES PATENT AND TRADEMARK OFFICE
CERTIFICATE OF CORRECTION

PATENT NO. : 7,528,155 B2
APPLICATION NO. : 11/042565
DATED : May 5, 2009
INVENTOR(S) : Gerhard Zoller et al.

Page 1 of 1

It is certified that error appears in the above-identified patent and that said Letters Patent is hereby corrected as shown below:

On the title page, in item (75), in column 1, in "Inventors", line 2, delete "Gunter Muller," and insert -- Günter Müller, --, therefor.

On the title page, in item (56), in column 2, under "Foreign Patent Documents", line 9, below "WO 2004/046090" delete "WO WO 2004/046090 6/2004".

In column 17, line 56-57, delete "methyl piperidine" and insert -- methylpiperidine --, therefor.

In column 18, line 15, delete "and 390" and insert -- 390 --, therefor.

Signed and Sealed this
Seventh Day of June, 2011

David J. Kappos
*Director of the United States Patent and Trademark Office*